US012766244B2

(12) United States Patent
Workman

(10) Patent No.: US 12,766,244 B2
(45) Date of Patent: Oct. 20, 2026

(54) AUTOMATIC SELECTION OF A DISPOSABLE INFUSION CONTAINER

(71) Applicant: CareFusion 303, Inc., San Diego, CA (US)

(72) Inventor: Michael K. Workman, Carlsbad, CA (US)

(73) Assignee: CAREFUSION 303, INC., San Diego, CA (US)

(*) Notice: Subject to any disclaimer, the term of this patent is extended or adjusted under 35 U.S.C. 154(b) by 383 days.

(21) Appl. No.: 18/692,780

(22) PCT Filed: Sep. 19, 2022

(86) PCT No.: PCT/US2022/044025
§ 371 (c)(1),
(2) Date: Mar. 15, 2024

(87) PCT Pub. No.: WO2023/044127
PCT Pub. Date: Mar. 23, 2023

(65) Prior Publication Data

US 2025/0135098 A1 May 1, 2025

Related U.S. Application Data

(60) Provisional application No. 63/246,262, filed on Sep. 20, 2021.

(51) Int. Cl.
*A61M 5/14* (2006.01)
*A61M 5/142* (2006.01)
(Continued)

(52) U.S. Cl.
CPC .......... *A61M 5/1413* (2013.01); *G16H 20/17* (2018.01); *G16H 40/67* (2018.01)

(58) Field of Classification Search
CPC .. A61M 5/1413; A61M 5/1407; A61M 5/142; A61M 5/158; A61M 5/16827;
(Continued)

(56) References Cited

U.S. PATENT DOCUMENTS

| | | | |
|---|---|---|---|
| 5,637,093 | A | 6/1997 | Hyman et al. |
| 5,713,856 | A | 2/1998 | Eggers et al. |

(Continued)

FOREIGN PATENT DOCUMENTS

| | | | |
|---|---|---|---|
| CN | 1561241 | A | 1/2005 |
| CN | 101360453 | A | 2/2009 |

(Continued)

OTHER PUBLICATIONS

Cardinal Health, (n.d.) Ivac Pcam Syringe Pump—Technical Service Manual, 1000SM00017, Issue 2 (2005-2006). 106 pages.

(Continued)

*Primary Examiner* — Jason E Flick
(74) *Attorney, Agent, or Firm* — MASCHOFF BRENNAN

(57) ABSTRACT

The subject technology provides for automatic selection of a disposable medication container during an infusion. A user interface configured to display a selectable list of disposables and configured for receiving a selection of a disposable from the selectable list for use in providing a therapy to a patient by the medical device. When an indication of a selected disposable is received, a first sensor or a motor associated with the medical device is adjusted to provide the therapy to the patient, according to a characterization of the selected disposable. Automated programming data configured to instruct an infusion device regarding an infusion of a medication is received from a server, and includes disposable information, including a selection of the disposable. The selectable list of disposables is then bypassed and not (Continued)

displayed when the automated programming data is received and selects the selected disposable.

20 Claims, 7 Drawing Sheets

(51) Int. Cl.
*A61M 5/168* (2006.01)
*G16H 20/17* (2018.01)
*G16H 40/67* (2018.01)

(58) Field of Classification Search
CPC .... A61M 2005/14208; A61M 2205/50; A61M 2205/502; A61M 2205/505; A61M 5/00; G16H 20/17; G16H 40/67; G16H 40/63; G16H 40/20; G16H 40/40
See application file for complete search history.

(56) References Cited

U.S. PATENT DOCUMENTS

| | | | |
|---|---|---|---|
| 5,781,442 | A | 7/1998 | Engleson et al. |
| 6,519,569 | B1 | 2/2003 | White et al. |
| 7,945,452 | B2 | 5/2011 | Fathallah et al. |
| 7,999,810 | B1 | 8/2011 | Boice et al. |
| 8,078,983 | B2 | 12/2011 | Davis et al. |
| 8,235,938 | B2 | 8/2012 | Eggers et al. |
| 8,359,338 | B2 | 1/2013 | Butterfield et al. |
| 8,435,206 | B2 | 5/2013 | Evans et al. |
| 8,486,019 | B2 | 7/2013 | White et al. |
| 8,553,039 | B1 | 10/2013 | Boice et al. |
| 9,177,108 | B2 | 11/2015 | Garibaldi et al. |
| 9,971,871 | B2 | 5/2018 | Arrizza et al. |
| 10,275,571 | B2 | 4/2019 | Coffman et al. |
| 10,625,015 | B2 | 4/2020 | Garibaldi et al. |
| 11,289,180 | B2 | 3/2022 | Vik et al. |
| 11,324,880 | B2 | 5/2022 | Garibaldi et al. |
| 11,901,058 | B2 | 2/2024 | Vik et al. |
| 12,028,414 | B1 | 7/2024 | Borges et al. |
| 12,121,696 | B2 | 10/2024 | Garibaldi et al. |
| 12,205,703 | B2 | 1/2025 | Vik et al. |
| 12,278,868 | B2 | 4/2025 | Borges et al. |
| 2002/0019714 | A1 | 2/2002 | Carliale et al. |
| 2002/0032429 | A1 | 3/2002 | Hjertman et al. |
| 2002/0038392 | A1 | 3/2002 | De La Huerga |
| 2002/0071076 | A1 | 6/2002 | Webb et al. |
| 2002/0099273 | A1 | 7/2002 | Bocionek et al. |
| 2002/0188259 | A1 | 12/2002 | Hickle et al. |
| 2002/0193679 | A1 | 12/2002 | Malave et al. |
| 2003/0009244 | A1 | 1/2003 | Engleson et al. |
| 2003/0069614 | A1 | 4/2003 | Bowman et al. |
| 2003/0139701 | A1 | 7/2003 | White et al. |
| 2003/0140928 | A1 | 7/2003 | Bui et al. |
| 2003/0140929 | A1 | 7/2003 | Wilkes et al. |
| 2003/0141981 | A1 | 7/2003 | Bui et al. |
| 2003/0144878 | A1 | 7/2003 | Wilkes et al. |
| 2003/0200117 | A1 | 10/2003 | Manetta et al. |
| 2004/0019464 | A1 | 1/2004 | Martucci et al. |
| 2004/0030323 | A1 | 2/2004 | Ullestad et al. |
| 2004/0032426 | A1 | 2/2004 | Rutledge et al. |
| 2004/0078231 | A1 | 4/2004 | Wilkes et al. |
| 2004/0167465 | A1 | 8/2004 | Mihai et al. |
| 2004/0167804 | A1 | 8/2004 | Simpson et al. |
| 2004/0172222 | A1 | 9/2004 | Simpson et al. |
| 2004/0172301 | A1 | 9/2004 | Mihai et al. |
| 2004/0172302 | A1 | 9/2004 | Martucci et al. |
| 2004/0176667 | A1 | 9/2004 | Mihai et al. |
| 2005/0010447 | A1 | 1/2005 | Miyasaka et al. |
| 2005/0038332 | A1 | 2/2005 | Saidara et al. |
| 2005/0055242 | A1 | 3/2005 | Bello et al. |
| 2005/0055244 | A1 | 3/2005 | Mullen et al. |
| 2005/0065817 | A1 | 3/2005 | Mihai et al. |
| 2005/0108057 | A1 | 5/2005 | Cohen et al. |
| 2005/0140498 | A1 | 6/2005 | Bastian, II |
| 2005/0171512 | A1 | 8/2005 | Flaherty |
| 2005/0267402 | A1 | 12/2005 | Stewart et al. |
| 2006/0026205 | A1 | 2/2006 | Butterfield |
| 2006/0081257 | A1 | 4/2006 | Krogh et al. |
| 2006/0098666 | A1 | 5/2006 | Francis Conde Powell |
| 2006/0167722 | A1 | 7/2006 | Mrf Struys et al. |
| 2006/0189926 | A1 | 8/2006 | Hall et al. |
| 2006/0206356 | A1 | 9/2006 | Vanderveen |
| 2006/0229557 | A1 | 10/2006 | Fathallah et al. |
| 2007/0041626 | A1 | 2/2007 | Weiss et al. |
| 2007/0098565 | A1 | 5/2007 | Parsee et al. |
| 2007/0124002 | A1 | 5/2007 | Estes et al. |
| 2007/0145137 | A1 | 6/2007 | Mrowiec |
| 2007/0210157 | A1 | 9/2007 | Miller |
| 2007/0233521 | A1 | 10/2007 | Wehba et al. |
| 2007/0251835 | A1 | 11/2007 | Mehta et al. |
| 2007/0254593 | A1 | 11/2007 | Jollota et al. |
| 2007/0258395 | A1 | 11/2007 | Jollota et al. |
| 2007/0267475 | A1 | 11/2007 | Hoglund et al. |
| 2008/0071251 | A1 | 3/2008 | Moubayed et al. |
| 2008/0086333 | A1 | 4/2008 | Hertel et al. |
| 2008/0125657 | A1 | 5/2008 | Chomas et al. |
| 2008/0148040 | A1 | 6/2008 | Machani et al. |
| 2008/0201169 | A1 | 8/2008 | Galasso et al. |
| 2008/0275422 | A1 | 11/2008 | Ross |
| 2008/0281167 | A1 | 11/2008 | Soderberg et al. |
| 2008/0294142 | A1 | 11/2008 | Patel et al. |
| 2009/0063402 | A1 | 3/2009 | Hayter |
| 2009/0069745 | A1 | 3/2009 | Estes et al. |
| 2009/0153058 | A1 | 6/2009 | Feng et al. |
| 2009/0156990 | A1 | 6/2009 | Wenger et al. |
| 2009/0156991 | A1 | 6/2009 | Roberts |
| 2009/0157040 | A1 | 6/2009 | Jacobson et al. |
| 2009/0157695 | A1 | 6/2009 | Roberts |
| 2009/0183105 | A1 | 7/2009 | Teel, IV et al. |
| 2009/0271729 | A1 | 10/2009 | Killoren Clark et al. |
| 2009/0275886 | A1 | 11/2009 | Blomquist et al. |
| 2010/0121170 | A1 | 5/2010 | Rule |
| 2010/0121654 | A1 | 5/2010 | Portnoy et al. |
| 2010/0160860 | A1 | 6/2010 | Celentano et al. |
| 2010/0271218 | A1* | 10/2010 | Hoag .................... A61M 5/142 358/1.15 |
| 2010/0292645 | A1 | 11/2010 | Hungerford et al. |
| 2011/0006876 | A1 | 1/2011 | Moberg et al. |
| 2011/0009813 | A1 | 1/2011 | Rankers |
| 2011/0009814 | A1 | 1/2011 | Tsoukalis |
| 2011/0029324 | A1 | 2/2011 | Kondo et al. |
| 2011/0072379 | A1 | 3/2011 | Gannon et al. |
| 2011/0238032 | A1 | 9/2011 | McTaggart et al. |
| 2011/0259954 | A1 | 10/2011 | Bartz et al. |
| 2011/0264044 | A1 | 10/2011 | Bartz et al. |
| 2012/0029941 | A1 | 2/2012 | Malave et al. |
| 2012/0215169 | A1 | 8/2012 | Moberg et al. |
| 2012/0220928 | A1 | 8/2012 | Estes et al. |
| 2012/0310152 | A1 | 12/2012 | Wehba et al. |
| 2012/0323090 | A1 | 12/2012 | Bechtel et al. |
| 2013/0047113 | A1 | 2/2013 | Hume et al. |
| 2013/0055106 | A1 | 2/2013 | Tarneberg et al. |
| 2013/0104120 | A1 | 4/2013 | Arrizza et al. |
| 2013/0138452 | A1 | 5/2013 | Cork et al. |
| 2013/0148532 | A1 | 6/2013 | Poon et al. |
| 2013/0152005 | A1 | 6/2013 | McLaren et al. |
| 2013/0185098 | A1 | 7/2013 | Mitchel et al. |
| 2013/0218080 | A1 | 8/2013 | Peterfreund et al. |
| 2013/0248426 | A1 | 9/2013 | Pouchoulin |
| 2013/0253946 | A1 | 9/2013 | Broselow |
| 2013/0283529 | A1 | 10/2013 | Hayes et al. |
| 2013/0317753 | A1 | 11/2013 | Kamen et al. |
| 2014/0039455 | A1 | 2/2014 | Miller et al. |
| 2014/0068487 | A1 | 3/2014 | Steiger et al. |
| 2014/0188516 | A1 | 7/2014 | Kamen et al. |
| 2014/0276560 | A1 | 9/2014 | Sehgal et al. |
| 2014/0323959 | A1 | 10/2014 | Lebel et al. |
| 2015/0154364 | A1 | 6/2015 | Biasi et al. |
| 2015/0356253 | A1 | 12/2015 | Sims et al. |
| 2015/0356255 | A1 | 12/2015 | Simpson et al. |
| 2016/0038163 | A1 | 2/2016 | Thor et al. |
| 2016/0103960 | A1 | 4/2016 | Hume et al. |
| 2017/0061083 | A1 | 3/2017 | Jackson |

(56) References Cited

U.S. PATENT DOCUMENTS

| | | | | |
|---|---|---|---|---|
| 2017/0128668 | A1 | 5/2017 | Miller et al. | |
| 2017/0255760 | A1 | 9/2017 | Lee et al. | |
| 2018/0193561 | A1 | 7/2018 | Susi | |
| 2019/0111209 | A1* | 4/2019 | Murphy, Jr. ............ | A61M 5/00 |
| 2020/0023127 | A1 | 1/2020 | Simpson et al. | |
| 2020/0051190 | A1 | 2/2020 | Kamen et al. | |
| 2020/0206413 | A1 | 7/2020 | Silkaitis et al. | |
| 2020/0357500 | A1 | 11/2020 | Rubalcaba, Jr. et al. | |
| 2021/0068683 | A1 | 3/2021 | Reich | |
| 2021/0146117 | A1 | 5/2021 | Reich et al. | |
| 2022/0001106 | A1 | 1/2022 | DiPerna et al. | |
| 2025/0032715 | A1 | 1/2025 | Dobbles et al. | |

FOREIGN PATENT DOCUMENTS

| | | | |
|---|---|---|---|
| CN | 102387217 | A | 3/2012 |
| JP | 2000042103 | A | 2/2000 |
| JP | 2005501340 | A | 1/2005 |
| JP | 2008535634 | A | 9/2008 |
| JP | 2009151806 | A | 7/2009 |
| JP | 2012128554 | A | 7/2012 |
| JP | 2013179973 | A | 9/2013 |
| WO | WO-03/019402 | A1 | 3/2003 |
| WO | WO-2005/086819 | A2 | 9/2005 |
| WO | WO-2006/110851 | A2 | 10/2006 |

OTHER PUBLICATIONS

Cardinal Health, (n.d.). IVAC Volumetric Pump—Models 597 & 598, Technical Service Manual, 1000SM0016, Issue 3 (1998-2006). 76 pages.

CareFusion Corporation and Cerner Corporation Integrate Smart Pump Technologies to Help Improve Medication Safety and Efficiency. Biospace. Webpage. (Apr. 19, 2012). 10 pages.

Defendants Baxter Intl and Baxter Healthcare's Opening Brief in Support of Their Motion to Dismiss for Failure to State a Claim, *Becton, Dickinson and Co et al.* v. *Baxter Intl, Inc et al.*, No. 1-25-cv-00591-CFC (D. Del. Jul. 10, 2025), ECF No. 18. 29 pages.

Defendants Baxter Intl and Baxter Healthcare's Reply Brief in Support of Their Motion to Dismiss for Failure to State a Claim, *Becton, Dickinson and Co et al.* v. *Baxter Intl Inc et al.*, No. 1-25-cv- 00591-CFC (D. Del. Aug. 29, 2025), ECF No. 31. 18 pages.

Defendants Baxter Intl and Baxter Healthcare's Motion to Dismiss for Failure to State a Claim, *Becton, Dickinson and Co et al.* v. *Baxter Intl Inc et al.*, No. 1-25-cv-00591-CFC (D. Del. Jul. 10, 2025), ECF No. 17. 4 pages.

Plaintiffs' Answering Brief in Opposition to Defendants' Motion to Dismiss Pursuant to Fed R. Civ. P. 12(b)(6), *Becton, Dickinson and Co et al.* v. *Baxter Intl, Inc et al.*, No. 1-25-cv-00591-CFC (D. Del. Aug. 11, 2025), ECF No. 26. 34 pages.

SIGMA International, Inc. (Aug. 2008). Sigma Spectrum Infusion Pump Service Manual. P/N 41019. (Rev. T). 56 pages.

SIGMA International, Inc. (Aug. 2009). Sigma Spectrum Infusion Pump Service Manual. P/N 41019. (Rev. W). 58 pages.

SIGMA International. (May 15, 2008). sigmaspectrum operator's manual. Sigma P/N 41018. (Rev. X). 63 pages.

SIGMA International. (Oct. 8, 2009). sigmaspectrum operator's manual. Sigma P/N 41018. (Rev. AL). 72 pages.

Sigma, LLC. (2010). sigmaspectrum Operator's Manual 35700ABB & 35700BAX. SIGMA Manual No. 41018. (Rev. AR). 102 pages.

SIGMA, LLC. (2010). sigmaspectrum Service Manual 35700ABB & 35700BAX. Sigma Manual No. 41019. (Rev. AA). 68 pages.

SIGMA, LLC. (2011). sigmaspectrum Operator's Manual 35700BAX & 35700ABB. Manual 41018-6.05/6.2.4. (Rev. C). 119 pages.

SIGMA, LLC. (2011). sigmaspectrum Operator's Manual 35700BAX & 35700ABB. Manual 41018-6.05/6.2.4. (Rev. D). 125 pages.

International Search Report and Written Opinion for Application No. PCT/US2022/044025, dated Jan. 16, 2023, 14 pages.

* cited by examiner

AUTOMATIC SELECTION OF A DISPOSABLE INFUSION CONTAINER

CROSS-REFERENCE TO RELATED APPLICATIONS

This is a National Stage Application, filed under 35 U.S.C. 371, of International Patent Application No. PCT/US2022/044025, filed on Sep. 19, 2022, which claims the benefit of U.S. Provisional Application No. 63/246,262, filed on Sep. 20, 2021, the entirety of each of which is incorporated herein by reference for all purposes.

BACKGROUND

This application relates generally to ensuring that an infusion device is properly programmed.

During an infusion of medication, the model type and size of a disposable medication container is fundamental for rate and volume accuracy. Syringe pumps are unable to reliably determine a disposable type and size purely by way of sensors. For example, outer diameters and heights overlap across multiple sizes and models. Consequently, clinicians manually enter the disposable model and size during the infusion programming workflow. However, this manual identification of syringe disposable can be prone to user error which in turn can affect the infusion pump and therapy administered thereby.

Medication orders often require more than one container of medication to complete. But multiple container orders are outside the visibility of the infusion pump, which resets the medication volume infused from one container to the next. The task of accumulating volumes across containers is left to the clinician and other data consumer applications. Moreover, a high priority alarm is currently mandated by some regulatory bodies (e.g., the U.S. Food and Drug Administrator) for "interruption of therapy" at the end of an infusion. However, alarms are often issued due to a clinician forgetting to hang the next container, which may be for the same order.

Modern infusion pumps provide, via a user interface, manual workflows with regard to programming infusion. In this regard, an infusion pump may receive infusion order parameters from a third-party system for pre-population, a process which is often referred to as an automated programming request (APR). However, APRs traditionally have not included data pertaining to disposable containers for delivery of medications used in infusions.

SUMMARY

The subject technology provides the container manufacturer, model, size, current container number, and total number of containers in the order to infusion devices during auto programming requests. Bypassing the manual selection process and automation of disposable selection eliminates the opportunity for user errors. Additionally, automatically receiving the data electronically (e.g., from the pharmacy management system) improves customer disposable usage.

Moreover, infusion devices configured according to the subject technology may accumulate volumes across containers, and for an entire pharmacy order for the patient. In this regard, alarms pertaining to near end and end of infusions are also improved. By receiving the total container count and the current container number, the infusion device may decide if the situation truly warrants a high priority alarm. Accordingly, nuisance alarms may be reduced or eliminated, and infusion status reporting is improved.

In this regard, the subject technology includes medical device, comprising: a display device; and a controller configured to: provide a user interface configured to display a selectable list of disposables and configured for receiving a selection of a disposable from the selectable list for use in providing a therapy to a patient by the medical device; adjust, when an indication of a selected disposable is received, a first sensor or a motor associated with the medical device to provide the therapy to the patient, according to a characterization of the selected disposable; and receive, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable. Other aspects include corresponding systems, methods, and computer program products for implementation of the corresponding device and its features.

The subject technology also relates to a method for mitigating automated programming request errors in a medical device. The method, performed by an infusion device, comprises: providing, a user interface configured to display a selectable list of disposables and configured for receiving a selection of a disposable from the selectable list for use in providing a therapy to a patient by the medical device; adjusting, when an indication of a selected disposable is received, a first sensor or a motor associated with the medical device to provide the therapy to the patient, according to a characterization of the selected disposable; and receiving, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable. Other aspects include corresponding systems, apparatus, and computer program products for implementation of the corresponding method and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

DESCRIPTION

Figure 1A:
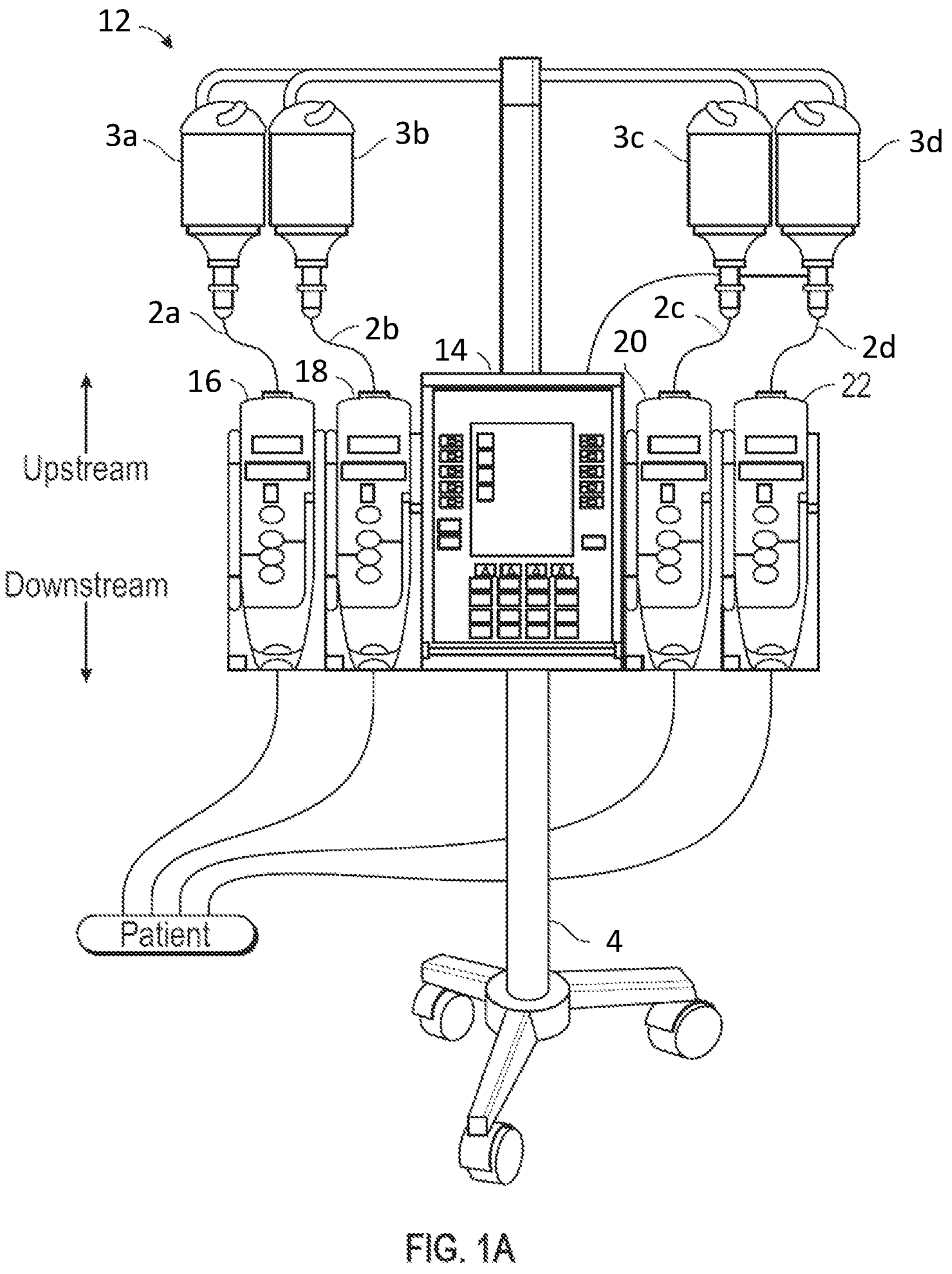
FIG. 1A depicts an example patient care system that includes an infusion device.

Reference will now be made to implementations, examples of which are illustrated in the accompanying drawings. In the following description, numerous specific details are set forth, in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

According to various implementations described herein, a medical device disposable can be physically connected to a medical device such as an infusion device, either directly or via an adapter or other mechanism. For example, the disposable can be a syringe, an infusion tubing set, or an adapter. Other disposables include devices used for chemotherapy, a syringe for manual administration of medication, epidural disposable, enteral disposable, per-enteral disposable as well as other types of equipment used to deliver fluid to a patient (in the case the case of infusion systems) or gas to a patient (in the case of ventilators). Different disposables may, for example, implicate different caregiving modalities. Disposables can be coded, for example, by a wireless tag (e.g., RFID, NFC, low energy Bluetooth™), a bar code, a quick read (QR) code, an optical code, or other, and identified by the infusion device and the infusion device can automatically switch to the appropriate configuration for providing care to the patient. For example, a tubing set that is coded for use with a neonate, would automatically switch the controls, alarms, settings, and other functions appropriate for a neonate rather than an adult.

In some implementations, detection of the coupling can occur when the disposable is being physically connected to the medical device or in physical proximity thereof. The physical connection can be detected, for example, using a switch which is mechanically tripped when the accessory is mechanically connected to the infusion device. Other technologies include integrated bar code scanners and other optical technologies, magnetic elements/switches, electromechanical element/switches, and the like. In some variations, the infusion device may include a proximity sensor that detect a corresponding signal from the accessory via electromagnetic fields/electromagnetic induction such as, Radio-Frequency Identification (RFID), Near Field Communication (NFC), and the like. In other variations, the infusion device may include an optical sensor that includes an optical sensor to scan or otherwise capture a visual identifier (e.g., bar code, optical pattern, etc.) on the disposable. Information about the disposable may be transmitted by these modalities.

When setting up an infusion by an infusion device, a clinician may scan a tag or badge associated with a patient, a disposable container of medication, and perform an association the patient and medication with an order in an electronic medical records (EMR) system. In such examples, the scanned information may be sent to one or more servers, which then collect information from the EMR system and initiates an automated programming request (APR). The APR is ultimately sent to and received by the infusion device, which programs itself based on information in the APR. The label or other transmitting device on the disposable container may include the patient's name, the medication in the container, and/or an order identifier. In some implementations, the information does not have the disposable characteristics in the label. The server gets the order information and collects other data, including disposable information, from various sources (e.g., a hospital information system). During that operation, the disposable type, manufacturer, and size may be retrieved and added to an APR. The server then sends this information to the infusion device as part of the APR.

According to various examples described herein, the infusion device (e.g., the syringe pump or system) may provide one or more user interfaces for selection of disposable characteristics, such as disposable type and size, both of which may be a precondition for programming the infusion device. In some examples, the infusion device may automatically perform measurements on the disposable when it is loaded by a user, and determine a list of possible disposable types, and display the types for selection by a user. On receiving a selection of a disposable from the user interface, the infusion device may program itself based on stored information corresponding to the selection and information in the APR. However, even having been presented with a list of possibilities, the chance of error still persists. According to various implementations described herein, the subject technology includes an automated process by which the selection step may be eliminated. In the case of a syringe pump, the APR may include information about the syringe type and/or size, thereby enabling the infusion device to auto-select the information and bypass the user interface for the selection process.

FIG. 1A is an example patient care system, according to various aspects of the subject technology. The patient care system 1 shown in FIG. 1A includes four fluid infusion pumps 16, 18, 20, 22, each of which is in operative engagement with a respective fluid administration set 2*a-d*. Fluid supplies 3*a-d*, which may take various forms but in this case are shown as bottles, are inverted and suspended above the pumps. Fluid supplies may also take the form of bags or other types of containers. Both the patient care system 1 and the fluid supplies 3*a-d* are mounted to a roller stand or pole 4. The specific fluid supplies as well as their orientation (e.g., mount location, mount height, mounting type, etc.) within the care area may generate one or more interaction records. The interaction record for a set for example may be generated in part by detecting a scannable code associated with the set or detecting a physical structure on the set that encodes identifying information for the set prior to use.

As shown in the example implementation of FIG. 1A, each administration set 2*a-d* is connected between a respective fluid supply 3*a-d* and the same patient so that the patient may receive the fluids in all the fluid supplies. The administration set may be identified either actively by, for example, scanning by a clinician or passively by, for example, wireless or optical detection of the administration set.

In the depicted example, a separate infusion pump 16, 18, 20, 22 is used to infuse each of the fluids of the fluid supplies into the patient. The infusion pumps are flow control devices that will act on the respective tube or fluid conduit of the fluid administration set to move the fluid from the fluid supply through the conduit to the patient. Because individual pumps are used, each may be individually set to the pumping or operating parameters required for infusing the particular medical fluid from the respective fluid supply into the patient at the particular rate prescribed for that fluid by the clinician.

Typically, medical fluid administration sets have more parts than are shown in FIG. 1A. Many have check valves, drip chambers, valved ports, connectors, and other devices well known to those skilled in the art. These other devices have not been included in the drawings so as to preserve clarity of illustration.

Figure 1B:
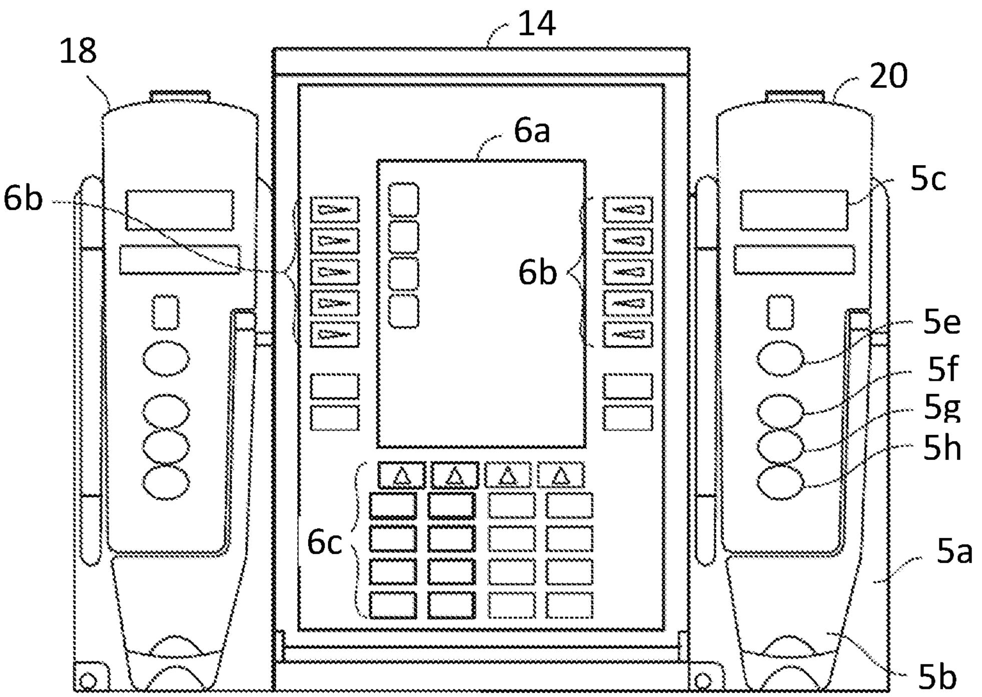
FIG. 1B depicts a closer view of a portion of the patient care system shown in FIG. 1A.

FIG. 1B is a closer view of a portion of the example patient care system shown in FIG. 1A, according to various aspects of the subject technology. FIG. 1B shows two of the fluid infusion pumps mounted at either side of a programming module, and the displays and control keys of each, with the programming module being capable of programming both infusion pumps. The infusion device 12 includes a door 5*a* and a handle 5*b* that operates to lock the door in a closed position for operation and to unlock and open the door for access to the internal pumping and sensing mechanisms and to load administration sets for the pump. When the door 5*a* is open, the tube can be connected with the pump 20. When the door 5*a* is closed, the tube is brought into operating engagement with the pumping mechanism, the upstream and downstream pressure sensors, and the other equipment of the pump. A display 5*c*, such as an LED display, is located in plain view on the door in this embodiment and may be used to visually communicate various information relevant to the pump 20, such as alert indications (e.g., alarm messages). Control keys 5*e-h* exist for programming and controlling operations of the infusion pump as desired. In some implementations, the control keys may be presented as interactive elements on the display 5*c* (e.g., touchscreen display). The infusion device 12 and/or infusion pump 20 may also include audio alert equipment in the form of a speaker (not shown).

The control unit 14 (also called a programming module or interface unit) of the infusion device 12 includes a display 6*a* for visually communicating various information, such as the operating parameters of a connected pump and alert indications and alert messages. The control unit 14 may also include a speaker to provide audible alerts. In some implementations, the display 6*a* may be implemented as a touchscreen display. In such implementations, the control keys 6*b* may be omitted or reduced in number by providing corresponding interactive elements via a graphical user interface presented via the display 6*a*. The control unit 14 may include a communications system (not shown) with which the control unit 14 may communicate with external equipment such as a medical facility server or other computer and with a portable processor, such as a handheld communication device or a laptop-type of computer, or other information device that a clinician may have to transfer information as well as to download drug libraries to a programming module 16, 18, 20, 22 (such as pump 20). The communication module may be used to transfer access and interaction information for clinicians encountering the programming module or device coupled therewith (e.g., pump 20 or bar code scanner). The communications system may include one or more of a radio frequency (RF) system, an optical system such as infrared, a BLUETOOTH™ system, or other wired or wireless system. The bar code scanner and communications system may alternatively be included integrally with the infusion pump 20, such as in cases where a programming module is not used, or in addition to one with the control unit 14. Further, information input devices need not be hard-wired to medical instruments, information may be transferred through a wireless connection as well. Additionally, other types of modules may be connected to the pump modules or to the programming module such as a syringe pump module, patient controlled analgesic module, End Tidal $CO_2$ monitoring module, oximeter monitoring module, or the like.

In some embodiments, the pressure measurements from the upstream and/or downstream pressure sensors are transmitted to a server or other coordination device, and the methods disclosed herein are implemented on the server or other coordination device. For example, more sophisticated and computationally intensive approaches like machine-learning can be implemented on the server (or on a PCU with a larger memory and/or CPU resources). In some embodiments, machine learning is used to identify syringe pump empty conditions based on pressure signals received from the pump.

Figure 1C:
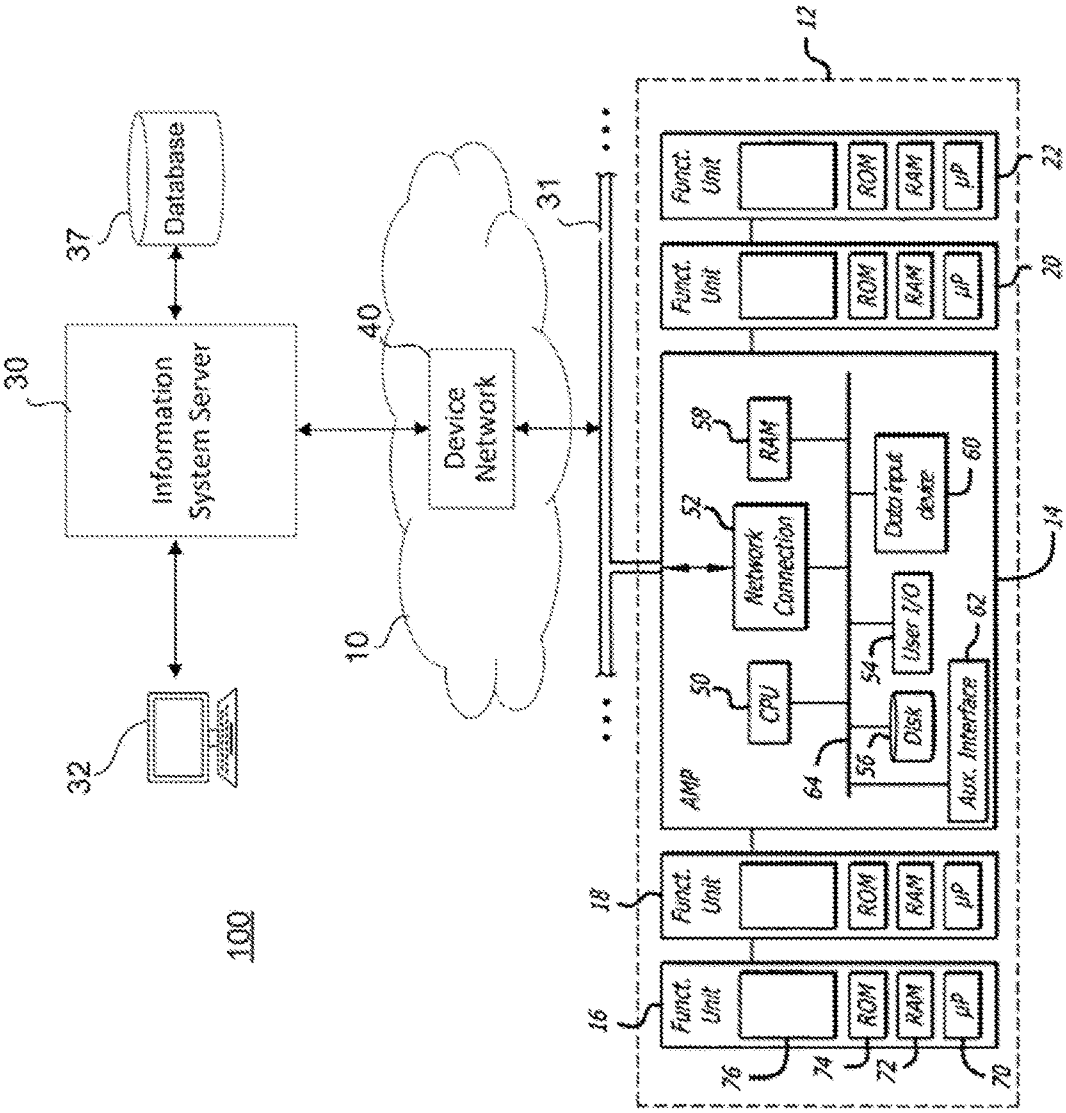
FIG. 1C depicts an example of an institutional patient care system of a healthcare organization, according to aspects of the subject technology.

FIG. 1C depicts an example of an institutional patient care system 100 of a healthcare organization, according to aspects of the subject technology. In FIG. 1C, a medical device (or "patient care device" generally) 12 is connected to a hospital network 10. The term medical device may be used interchangeably with the terms "patient care device" (or "PCD") or patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1C optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which medical devices 12 (and other devices) communicate in accordance with normal operations.

Additionally, institutional patient care system 100 may incorporate a separate information system server 130, the function of which will be described in more detail below. Moreover, although the information system server 130 is shown as a separate server, the functions and programming of the information system server 130 may be incorporated into another computer, if such is desired by engineers designing the institution's information system. Institutional patient care system 100 may further include one or multiple device terminals 132 for connecting and communicating with information system server 130. Device terminals 132 may include personal computers, personal data assistances, mobile devices such as laptops, tablet computers, augmented reality devices, or smartphones, configured with software for communications with information system server 130 via network 10.

Medical device 12 comprises a system for providing patient care, such as that described in Eggers et al., which is incorporated herein by reference for that purpose. Medical device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, medical device 12 comprises a control module 14, also referred to as control unit 14, connected to one or more functional modules 116, 118, 120, 122. Control unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Control unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally, or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally, or in the alternative, data input device 60 can be any device for entering coded data into a computer, such as a device(s) for reading magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1C to be disposed within control unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 116, 118, 120 and 122, and configured to communicate with controller 14, or any other system on the network, using suitable programming and communication protocols.

Network connection 52 may be a wired or wireless connection, such as by Ethernet, Wifi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1C, at least one of functional modules 16, 18, 20, 22 may be an infusion pump module such as an intravenous infusion pump for delivering medication or other fluid to a patient. For the purposes of this discussion, functional module 116 is an infusion pump module. Each of functional modules 16, 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like. Functional module 16, 18, 20 and/or 22 may be a printer, scanner, bar code reader, near-field communication reader, RFID reader, or any other peripheral input, output or input/output device.

Each functional module 16, 18, 20 and/or 22 communicates directly or indirectly with control unit 14, with control unit 14 providing overall monitoring and control of device 12. Functional modules 16, 18, 20 and/or 22 may be connected physically and electronically in serial fashion to one or both ends of control unit 14 as shown in FIG. 1C, or as detailed in Eggers et al. However, it is recognized that there are other means for connecting functional modules with the control unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate control unit or control unit 14. As described above, additional medical devices or peripheral devices may be connected to medical device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1C, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 116.

While each functional module may be capable of a least some level of independent operation, control unit 14 monitors and controls overall operation of device 12. For example, as will be described in more detail below, control unit 14 provides programming instructions to the functional modules 16, 18, 20, 22 and monitors the status of each module.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, medical device 12 and network 10 may communicate via automated interaction, manual interaction, or a combination of both automated and manual interaction. Automated interaction may be continuous or intermittent and may occur through direct network connection 54 (as shown in FIG. 1C), or through RS232 links, MIB systems, RF links such as BLUETOOTH, IR links, WLANS, digital cable systems, telephone modems or other wired or wireless communication means. Manual interaction between medical device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in health information system (HIS) server 30, decision support 48, remote data server 49, hospital department or unit stations 46, or within medical device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

With further reference to FIG. 1C, medical device 12 is capable of operating in several different modes, or personalities, with each personality defined by a configuration database. The configuration database may be a database 56 internal to the medical device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a medical device's 10 location in the hospital or hospital computer network. Patient care information may be entered through interface device 52, 54, 60 or 62, and may originate from anywhere in network 10, such as, for example, from a pharmacy server, admissions server, laboratory server, and the like.

A memory 56, 58 of the control unit 14 may contain the drug library or libraries, an event log or logs, and pump configuration settings, such as, but not limited to, profiles to be used in particular practice areas such as ICU, PED, etc. The memory may be electronically loadable memory such as non-volatile memory (e.g. EEPROM). Drug libraries, which illustratively contain such information as the drug names, ranges of delivery parameter values such as proper concentrations, dosage units, and dose limits, and can be used to perform drug calculation-based infusions.

The drug library stored within the infusion device's memory may include limits set by the clinical institution for each drug of the library (also termed as "guardrails" herein). Such limits may take the form of maximum and minimum dosages for each drug which may be made dependent on patient factors or other factors associated with delivery of the drug. For example, the dosage limits may vary depending on the weight of the patient or body surface area ("BSA"), depending on the unit or ward of the medical institution in which the drug is being used (for example neonatal care unit (NCU), the intensive care unit (ICU), etc.), and depending on other factors. An alarm may be provided if the nurse sets the infusion device to operate outside the range between the limits for a particular drug. In some cases, the alarm may be overridden and in other cases it may not. The medical facility may establish "soft" limits for each drug, which may be overridden by the nurse, and "hard" limits which may not. In either case where a limit is exceeded, a pump data log or other processor in communication with the infusion device may record each such limit event for later analysis where the attempted setting is higher than the maximum or lower than the minimum dosage.

The infusion device may also include a display for displaying a user interface, including a control panel through which the user can program the programmable controller and a display screen for displaying drug entries from the drug library. Each of the associated sets of drug delivery parameters includes information selected from a group of parameters including drug concentration, drug delivery rate, drug dose, and bolus size. The electronically loaded drug library contains a list of available mode options specifying the units available for expressing drug delivery information, and the infusion device offers the user the list of available mode options from which to make a selection when the electronically loaded drug library is stored in a memory of the infusion device. In the case of a syringe pump, the electronically loaded drug library may include a list of names of syringe manufacturers identifying syringes that can be used in the pump, and the pump offers the user the list of names of syringe manufacturers from which to make a selection when the electronically loaded drug library is in the pump.

The loaded drug library may include a list of syringe sizes identifying syringes that can be used in the pump, and the pump offers the user the list of syringe sizes from which to make a selection when the electronically loaded drug library is in said pump. In the case of a peristaltic pump, the electronically loaded drug library may include a list of infusion set manufacturers. A loaded drug library may include a set of features, each of which is either be toggled on or off, and the pump offers the user only the features from among the set of features that are toggled on when the electronically loaded drug library is in said pump.

Figure 2:
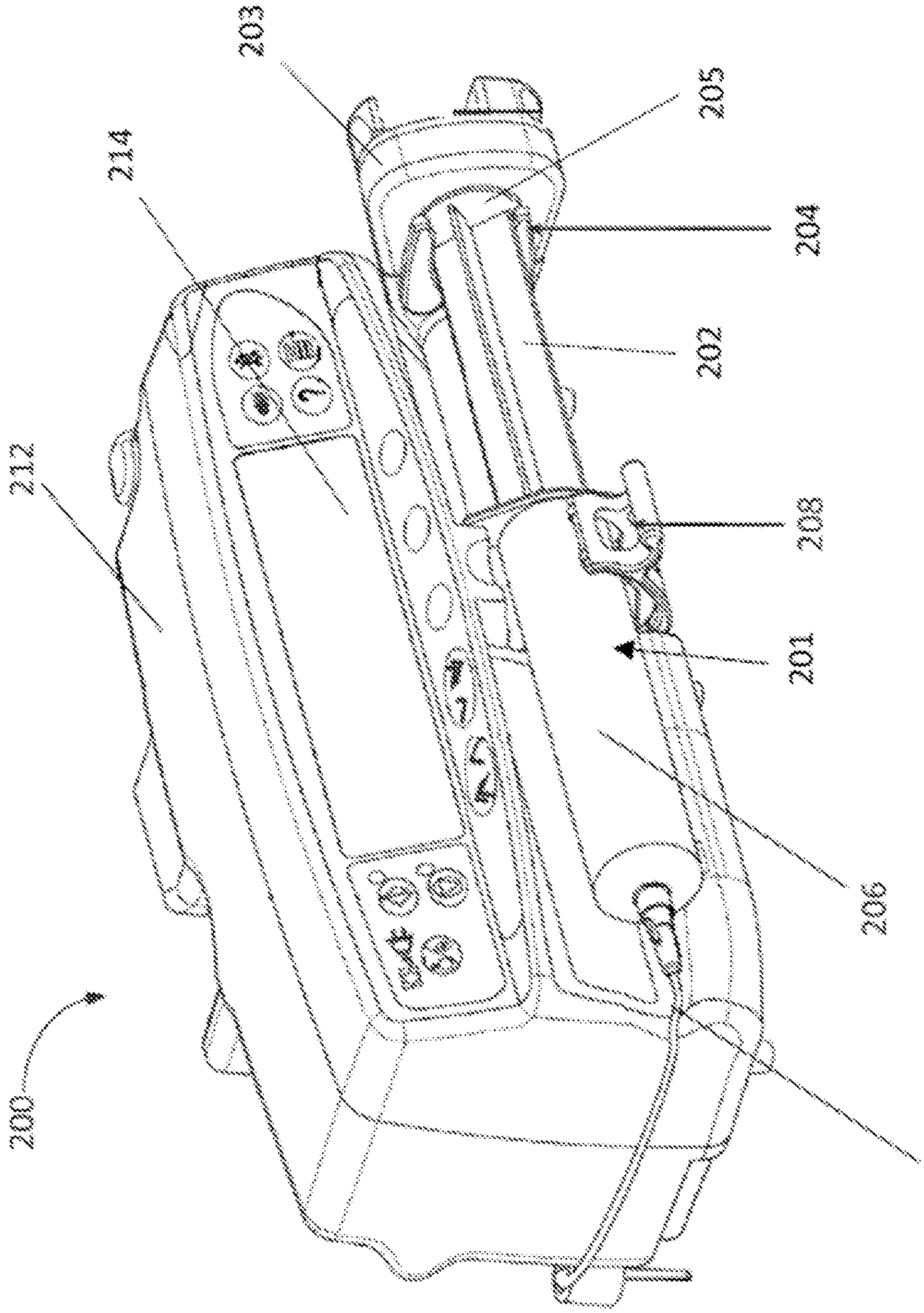
FIG. 2 depicts an example syringe infusion pump, according to aspects of the subject technology.

FIG. 2 shows an example syringe pump 200 infusion device, according to various aspects of the subject technology. While the example syringe pump 200 is shown as a stand alone device, the syringe pump may be configured as a functional module 16, 18, 20, 22 for operable connection to and/or coupling with a control unit 14 of the previously described medical device.

When a syringe 201 is mounted in the syringe pump 200 properly, a plunger flange at the end of the syringe piston 202 is held in a plunger drive head 203 with a pair of pivotally mounted plunger retaining arms. The syringe 206 is secured by a syringe clamp 208. The drive head 203 includes a pushing surface on which the plunger flange will rest as the drive head 203 moves forward toward the plunger barrel 206 pushing the plunger piston 202 into the barrel 206 of the syringe to expel the syringe contents through an administration tubing 210 to the patient. The drive head may be connected to a screw drive mechanism, including a motor, for connecting the linear motion of the screw drive mechanism to the syringe plunger in order to empty the syringe. The rate is controlled by the syringe pump 200 based on the programmed parameter (e.g., desired rate) and type of syringe.

Syringe pumps do not typically experience any upstream pressure conditions because the fluid to be infused is housed in the syringe barrel 206 and is pushed into an administration set 210 by way of the plunger 202. Downstream pressure conditions can be detected by a force sensor housed in or upon a pump system 212 according to the methods described here, which are readily applied to syringe pumps. The force sensor measures the force exerted by the drive head 203 of the syringe pump on the syringe piston 202.

In some embodiments, the syringe pump may include a high resolution pressure sensor that interfaces with a pressure disc (not shown) on the syringe administration set. The pressure disc provides a relatively large area in contact with the pressure sensor. This allows the pressure sensor to measure the pressure inside the administration set more directly (not through the syringe plunger head) and with higher resolution and higher accuracy compared with the drive head force sensor. The measurements from this pressure sensor and the drive head force sensor can be used independently or in conjunction with each other to detect an empty condition in a syringe pump.

In an infusion pump, various components that lie in an infusion path such as administration set, cannula, filters, and valves exhibit both resistance and compliance. In normal operation, the pump generates a pressure, termed a working pressure, to overcome the resistance of these and other components in the infusion path.

As well as operating buttons or switches, which the operator may use to activate and program the syringe pump 200, there is a display screen 214. The display screen 214 may be a simple LCD (liquid crystal display) having a small number of segments, for example seven segments in a figure-of-eight configuration per character, adapted to display a small number of alphanumeric characters. The display may be monochromatic, for example, it might only display red, green or grey/black characters. Alternatively, the display 214 might be a more complicated liquid crystal display capable of displaying more characters or more complicated characters. The LCD may be backlit, for example, using light emitting diodes (LEDs). In some implementations, the infusion pump may include a TFT LCD. A TFT is a thin-film transistor-based LCD technology. In some implementations, the display screen 214 is also a touchscreen such as a capacitative touchscreen.

When programming an infusion device, the user must input the type of syringe being fitted to the pump. The pump stores in an internal memory a database of known syringe types containing information such as syringe diameter and stroke. The infusion pump firmware calculates the position of the syringe plunger and syringe piston based on movement of the syringe driver head and the type and size of the syringe. This allows the machine to display the calculation of volume infused, time elapsed, volume remaining and time remaining. As infusion continues and the driver head moves, these calculations can be updated, and the displayed information changed.

Infusion pump may be provided with a scrolling system comprising an “up” scroll key and a “down” scroll key which are operable to increase or decrease pumping parameters, such as the mass flow rate setting shown on a display, or the VTBI (volume to be infused) setting shown on the display. In some cases, each scroll key may be physically present on the device (as depicted), or may be graphically displayed in a touchscreen display 214.

Figure 3:
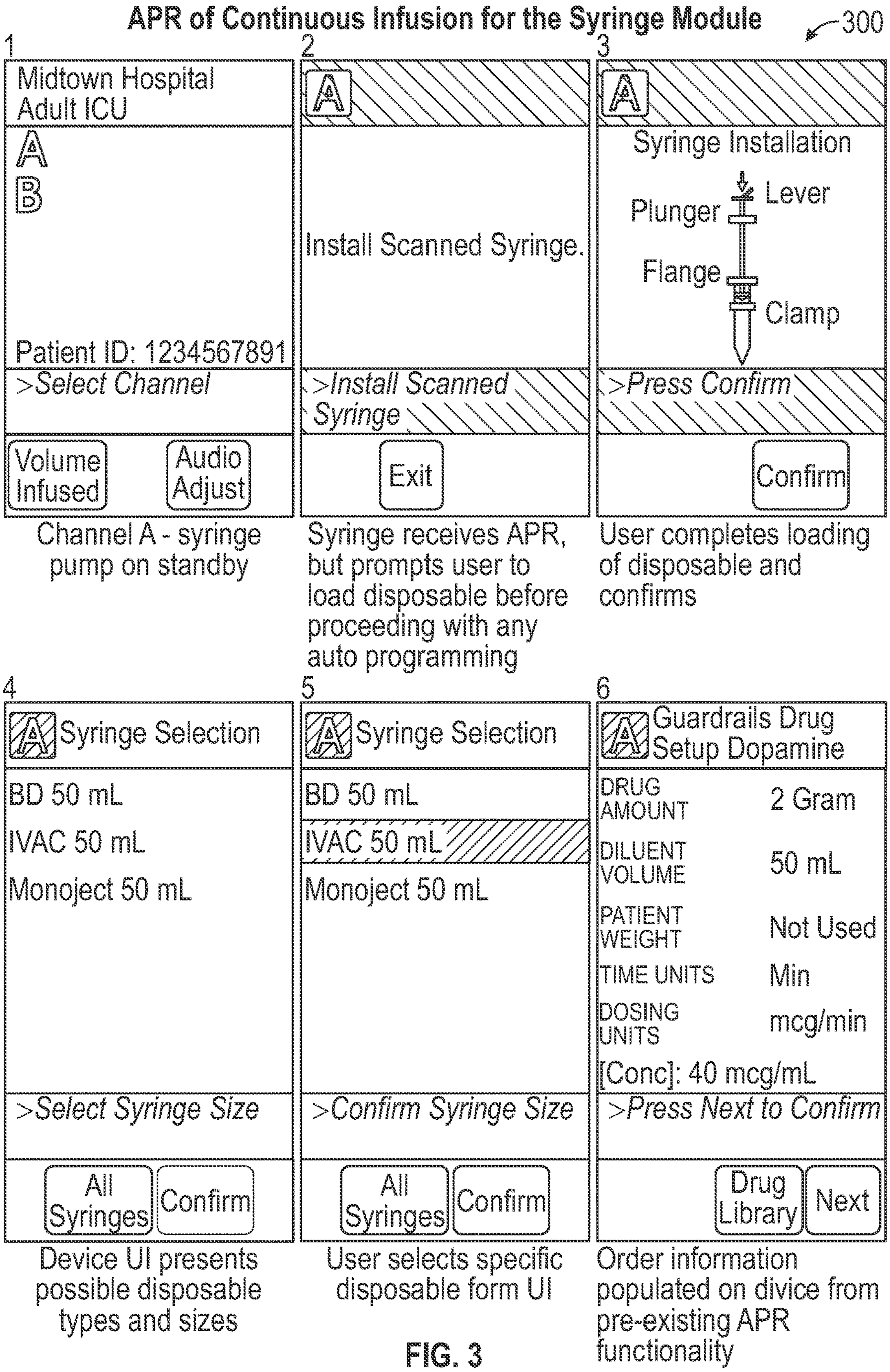
FIG. 3 depicts an example user interface for an example infusion programming workflow for a syringe pump, according to various aspects of the subject technology.

FIG. 3 depicts an example user interface for an example infusion programming workflow for a syringe pump, according to various aspects of the subject technology. The depicted screens 300 may be displayed on the display 214 of a syringe pump or a display **6*a* of connected control unit 14. In the depicted example workflow, a series of screens are displayed to facilitate selection of a particular syringe to be loaded into a syringe pump 200**.

The first screen depicts the pump 200 in a standby mode, with an option for the clinician to select between pump channels “A” or “B”. The clinician proceeds to select a channel for the infusion and scans a disposable syringe for use in the infusion. On selection of a channel—Channel “A” in the second example screen—the system (including, e.g., software operating on a computing device local to clinician) automatically sends a request to the server 30 for an APR. The system may send a previously scanned patient identifier in addition to information from a scanning of the disposable syringe. The syringe pump 200 (or control unit 14) may receive the APR from the server 30 and then prompt the clinician to load the syringe. Screen three depicts instructions for loading the syringe and provides a control to confirm the loading.

When a disposable syringe is manually loaded into a syringe pump, the syringe pump (or processor associated with the pump) may perform certain measurements on the syringe, including barrel size, height and other characteristics, and then determine a list of possible syringes based on information stored in its internal database. As depicted in the fourth example display screen, the list of possible syringe types may be displayed based on the measurements performed by the syringe pump. The clinician may then review the list and select and confirm one of the listed syringes. The fifth example display screen provides for selection of a syringe from the list. Once the syringe is selected, information from the drug library corresponding to the selected syringe and APR is loaded and provided for review by the clinician in the sixth screen. At this point, the infusion may be activated but not yet started. The clinician may review the information, make changes within the user interface, and confirm the start of the infusion.

According to various implementations, when the information regarding the patient and/or the medication is sent to the server 30, the server may query other systems based on the information. The server may, for example, retrieve the medication order for the patient, which may include a syringe type, barrel size, syringe manufacturer, model, and total number of containers in the order. This information is then packaged in the APR, which is downloaded to the infusion device. In some implementations, the APR may include current container number, for example if there have been several orders for the same medication or when multiple infusions may span several infusion devices. In some implementations, the syringe pump may maintain a current container number based on how many syringes have been loaded and administered for an order.

Accordingly, instead of forcing the user to select the syringe type, the subject technology sends information that would normally be entered by the clinician to the infusion device via the APR. The clinician scans the patient identifier and/or medication identifier, which is then sent to the server. The server pulls the order for the patient, confirms the medication from the order, and determines the syringe type, barrel size, syringe manufacturer, model, and total number of syringes in the order (and/or number). These selections enable the infusion device to bypass display screens four and five in the user interface depicted in FIG. 3.

In some implementations, instead of a list of possible syringes, the syringe obtained via the APR may be displayed with a prompt for the clinician to confirm the selection. If the clinician confirms the selection, then the syringe pump is configured according to the APR. If the auto-selection is not confirmed, then a list of possible syringe types may be displayed based on the measurements performed by the syringe pump.

The automatic container identification features of the subject technology can drive additional or alternative functions on the pump such as force detectors, occlusion detectors (e.g., detection thresholds), and the speed of the motor. For example, the amount of force that is detected by the drive head may be indicative of whether an occlusion is present. Depending on the size of the syringe barrel or differences in syringe design or manufacturing (e.g., materials, shape, plunger arrangement, etc.) the threshold amount of force for detecting the occlusion may be higher or lower. Based on the container information in the APR, the syringe pump may automatically adjust the threshold force for detecting an occlusion, and/or automatically adjust the motor speed to obtain a predetermined flow rate for the barrel size.

Figure 4:
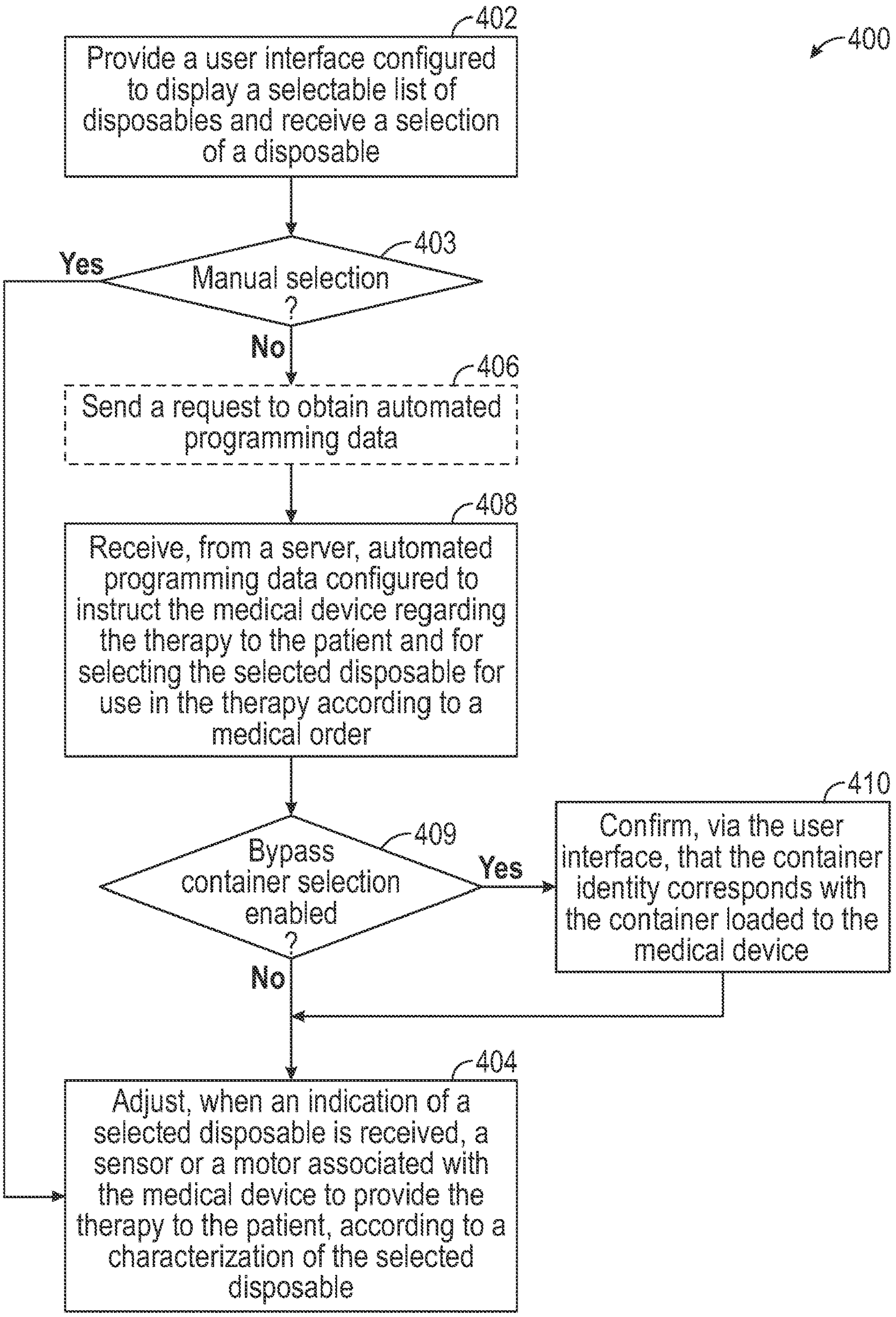
FIG. 4 depicts an example process for automatically programming a medical device, including bypassing portions of an infusion programming workflow, according to aspects of the subject technology.

FIG. 4 depicts a second example process for automatically programming a medical device, including bypassing portions of an infusion programming workflow, according to aspects of the subject technology. For explanatory purposes, the various blocks of example process 400 are described herein with reference to FIGS. 1A, 1B, 1C, and 2, and the components and/or processes described herein. The one or more of the blocks of process 400 may be implemented, for example, by one or more computing devices including, for example, medical device 12. In some implementations, one or more of the blocks may be implemented based on one or more machine learning algorithms. In some implementations, one or more of the blocks may be implemented apart from other blocks, and by one or more different processors or devices. Further for explanatory purposes, the blocks of example process 400 are described as occurring in serial, or linearly. However, multiple blocks of example process 400 may occur in parallel. In addition, the blocks of example process 400 need not be performed in the order shown and/or one or more of the blocks of example process 400 need not be performed.

In the depicted example, a medical device 12 provides a user interface configured to display a selectable list of disposables (see FIG. 3) and configured for receiving a selection of a disposable from the selectable list for use in providing a therapy to a patient by the medical device (402). As described previously, the medical device may be or include an infusion pump and the therapy may include an infusion of a fluid such as a medication. According to various implementations, the medical device may be a syringe pump, such as that depicted in FIG. 2.

The clinician may then, via the user interface, choose to manually select a disposable from the list (403). When an indication of a selected disposable is received (e.g., by way of the manual selection), the medical device adjusts a sensor or a motor associated with the medical device to provide the therapy to the patient, according to a characterization of the selected disposable (404). The sensor may include a force sensor that measures a pressure in an infusion line, or measures a force exerted by a drive head of a syringe pump 200. The motor may include a peristaltic mechanism in implementations where the medical device is a peristaltic pump, and may include a motor that drives the drive head in implementations, where the medical device is a syringe pump.

In the depicted example, a request to obtain automated programming data (e.g., an APR) is (optionally) sent to the server 30 (406). One example of how the request to obtain the automated programming data may include, for example, the infusion device system (e.g., a processor within the device or a supporting system) receiving scanned information from a medication container that was scanned by a scanner associated with the infusion device, and sending the scanned information to the server with a request to obtain the automated programming data.

According to various implementations, the medical device is configured to display the selectable list of disposables in the user interface when the automated programming data selecting the selected disposable is not received by the medical device. However, the display screen prompting for selection of a disposable from a selectable list of disposables may be bypassed and not displayed when the automated programming data is received and selects the selected disposable. In such instances, portions of an infusion programming workflow are bypassed, preserving memory space and interface resources, and removing an opportunity for operator error.

In the depicted example, the infusion device 12 receives, from the server 30, automated programming data configured to instruct the medical device regarding the therapy to the patient and for selecting the selected disposable for use in the therapy according to a medical order for the patient (408). In some implementations, the automated programming data instructs an infusion device regarding an infusion of a medication (e.g., the scanned medication). The automated programming data may be in the form of a programming request and may include, for example, a drug identifier and a request to load parameters for a drug corresponding to the drug identifier. As described above, an APR may instruct the infusion device to load the parameters from an available drug library stored on the infusion device. According to various implementations, the APR may include the characterization of the selected disposable and/or other disposable information for a disposable selected to administer a fluid in accordance with the medical order. In some implementations, the server 30, having been in communication with a device 12, may send the programming data without a request being first sent to the server, as described above.

In some implementations, the infusion device 12 may be configured to require confirmation of the container selection received via an APR (409). In such implementations, when the container selection is received via an APR, the system may prompt, via the user interface, the clinician to confirm that the container identity corresponds to with the container loaded in the infusion device. Once confirmed, the infusion device 12 proceeds with operations as if the container was selected manually.

As described previously, when the automated programming data is received by a medical device such as an infusion pump—or control unit 14 associated with the infusion pump—the medical device automatically adjusts a motor speed of the motor when the automated programming data selects the selected disposable (404). Accordingly, the motor speed may be automatically adjusted based on the characterization of the selected disposable to satisfy a predetermined flow rate for the infusion. In implementations, where the medical device is a syringe pump, the characterization received in the automated programming data may include a size of a syringe to be used for the infusion. In this regard, the motor speed may be automatically adjusted to control a speed of a syringe plunger based on the size of the syringe.

In some implementations, the automated programming data includes a number of medication containers to fulfill a medication order associated with the patient. An infusion device 12 may be configured to maintain a status of each infusion and each container with regard to the size, amount in the syringe, the syringe number within a group, and the total amount of medication infused for the particular order. Accordingly, the infusion device 12 may automatically determine a current container number of a medication container loaded by the infusion device. When the medication within the medication container has been administered to the patient, the infusion device 12 may determine, based on the current container number and the number of medication containers to fulfill the medication order, that a second container should be loaded by the infusion device, and provide a user prompt, for display by the display device 6*a* or 214, to confirm loading of the second container. In other words, when a container becomes empty, if the total amount of medication for the order has not yet been infused and/or the current container is not the last container of a group then the infusion device 12 will not initiate a high priority alarm. Instead, the infusion device 12 may display that the container is empty, the number of containers left to infuse, and prompt the clinician to load the next container. At the end of the order, the alarm may be disabled and no further alarm for an empty container may be provided.

As described previously, the infusion device 12 may be configured to identify (e.g., using a sensor) a disposable container loaded by the device. For example, a syringe pump 200 may perform electro-mechanical measurements on the loaded syringe to identify certain characteristics about the loaded container. For example, a syringe pump may include a sensor that measures the size of the syringe inserted into the pump, for example, based on how tightly the syringe is being hugged. The clock position may determine the size of the barrel (e.g., whether it is a 6, 10, 50 ml syringe, etc.). Each syringe pump may include a drive head 203 that pushes up against a flange clamp 204 (see FIG. 2). When the clamp 204 comes down on the flange 205 of the piston 202 then the size of the flange 205 can be determined. Based on the physical measurements made by the pump, the syringe pump may determine a list of possible candidate syringes. The device may then determine whether the container provided in the APR is within that list. The infusion device may initiate an alarm indicating that the container loaded into the pump deviates from the scanned syringe.

Based on the selected disposable selected by the automated programming data, the infusion device is capable of determining whether the disposable container loaded by the infusion pump deviates from the selected disposable. If a deviation is found, then an indication of the deviation may then be displayed on the display 6*a* or 214 of the device. More specifically, in some implementations, the size of the disposable container loaded by the infusion pump may be determined. For example, a barrel size of a syringe loaded by a syringe pump 200 may be determined. The infusion device 12 may then determine that the measured size of the disposable container does not match the received size of the selected disposable and, which a deviation is detected, display the indication of the deviation.

In another example, a clinician may scan a medication label on a disposable and load the disposable in a medical device before the APR is received by the medical device. With the disposable manufacture and size as well as the VTBI received in the APR, the device can then determine if the disposable is already loaded, or is yet to be loaded. If it is already loaded, then the selection of the disposable may be automated without further confirmation by the user. If the disposable is not yet loaded, then the device may prompt or remind the user to load the disposable.

In some instances, when a syringe loaded in a syringe pump 200 is different than a syringe specified in the APR, or otherwise different in size, the system may determine whether there is enough volume in the disposable to complete or come close to the VTBI (volume to be infused), for example, within a threshold tolerance. If the loaded syringe is compatible (and, e.g., of the same medication) then the system may prompt the clinician to confirm use of the loaded syringe, and the syringe pump may complete the order with the currently loaded syringe. Additionally, or in the alternative, if the currently loaded disposable volume cannot satisfy the VTBI (e.g, by way being partially full or empty at a lower size) then the system may require the clinician to identify another syringe for completion of the order (e.g., by scanning another container).

The adjustment corresponding to an identified syringe or container may be identified using a look up table indexed by, for example, the syringe identifier. The look up table may include specific values or ranges of values for detectors or motor speed. In some implementations, determining an adjustment may be based on properties of the container. For example, an equation or other model may be stored in the memory of the infusion device. The model may receive input values corresponding to properties of the syringe such as barrel diameter, barrel length, average or estimated stiction, syringe tip diameter, etc. The model may generate an output identifying the configuration value for the infusion pump such as the detection threshold. In some implementations, the model may also consider the state of the infusion. For example, the detection threshold may change based on a quantity of fluid delivered such that the threshold used to monitor the start of an infusion may be different than a threshold used to monitor the end of the infusion.

Many of the above-described example process 400, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 5:
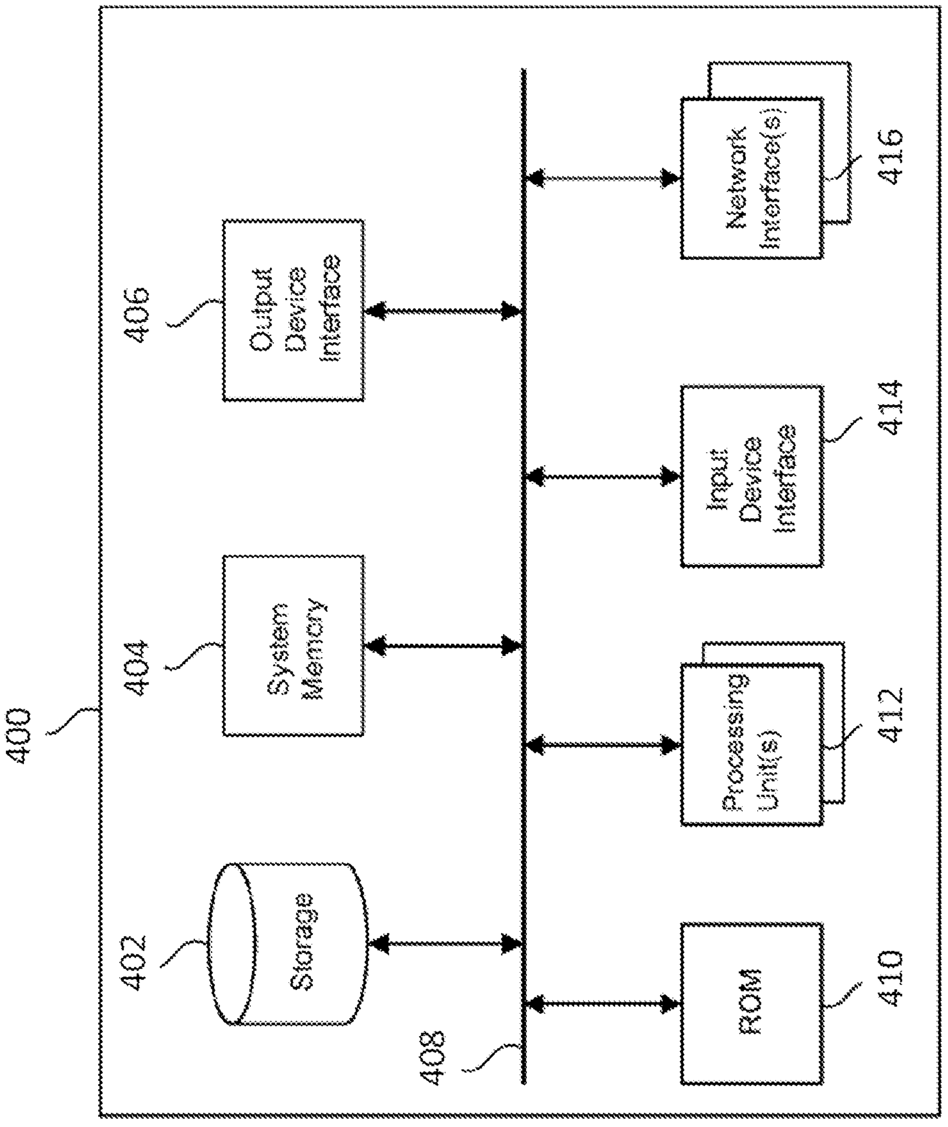
FIG. 5 is a conceptual diagram illustrating an example electronic system for automatically programming a medical device, including bypassing portions of an infusion programming workflow, according to aspects of the subject technology.

FIG. 5 is a conceptual diagram illustrating an example electronic system 400 for automatically programming a medical device, including bypassing portions of an infusion programming workflow, according to aspects of the subject technology. Electronic system 500 may be a computing device for execution of software associated with one or more portions or steps of process 400, or components and methods provided by FIGS. 1-4, including but not limited to computing hardware within medical device 12, and/or any computing devices or associated terminals disclosed herein. In this regard, electronic system 400 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 500 may include various types of computer readable media and interfaces for various other types of computer readable media. In the depicted example, electronic system 500 includes a bus 508, processing unit(s) 512, a system memory 504, a read-only memory (ROM) 510, a permanent storage device 502, an input device interface 514, an output device interface 506, and one or more network interfaces 516. In some implementations, electronic system 500 may include or be integrated with other computing devices or circuitry for operation of the various components and methods previously described.

Bus 508 collectively represents all system, peripheral, and chipset buses that communicatively connect the numerous internal devices of electronic system 500. For instance, bus 508 communicatively connects processing unit(s) 512 with ROM 510, system memory 504, and permanent storage device 502.

From these various memory units, processing unit(s) 512 retrieves instructions to execute and data to process, in order to execute the processes of the subject disclosure. The processing unit(s) can be a single processor or a multi-core processor in different implementations.

ROM 510 stores static data and instructions that are needed by processing unit(s) 512 and other modules of the electronic system. Permanent storage device 502, on the other hand, is a read-and-write memory device. This device is a non-volatile memory unit that stores instructions and data even when electronic system 500 is off. Some implementations of the subject disclosure use a mass-storage device (such as a magnetic or optical disk and its corresponding disk drive) as permanent storage device 502.

Other implementations use a removable storage device (such as a floppy disk, flash drive, and its corresponding disk drive) as permanent storage device 502. Like permanent storage device 502, system memory 504 is a read-and-write memory device. However, unlike storage device 502, system memory 504 is a volatile read-and-write memory, such as, random access memory. System memory 504 stores some of the instructions and data that the processor needs at runtime. In some implementations, the processes of the subject disclosure are stored in system memory 504, permanent storage device 502, and/or ROM 510. From these various memory units, processing unit(s) 512 retrieves instructions to execute and data to process, in order to execute the processes of some implementations.

Bus 408 also connects to input and output device interfaces 514 and 506. Input device interface 514 enables the user to communicate information and select commands to the electronic system. Input devices used with input device interface 514 include, e.g., alphanumeric keyboards and pointing devices (also called "cursor control devices"). Output device interfaces 506 enables, e.g., the display of images generated by the electronic system 500. Output devices used with output device interface 506 include, e.g., printers and display devices, such as cathode ray tubes (CRT) or liquid crystal displays (LCD). Some implementations include devices such as a touchscreen that functions as both input and output devices.

Also, as shown in FIG. 5, bus 508 also couples electronic system 500 to a network (not shown) through network interfaces 516. Network interfaces 516 may include, e.g., a wireless access point (e.g., Bluetooth or WiFi) or radio circuitry for connecting to a wireless access point. Network interfaces 516 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 500 can be used in conjunction with the subject disclosure.

These functions described above can be implemented in computer software, firmware, or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Although the discussion references the use of container information within an APR to improve the accuracy and safety of device configuration, the features may be implemented in other medical devices that currently include a container selection. For example, an intravenous compounding device may include selection of a container into which a medication will be compounded. The selection is typically performed manually or, in some instances, based on image recognition. Similar to the faults that can arise discussed above, manual entry or image recognition can misidentify containers. The misidentification may impact further processes of the compounding system such as identification of tare weight, container compatibility with drugs or components included in the preparation, volumetric verification of the preparation, and the like. Accordingly, such systems may receive container information as part of the order to compound a medication or other workflow including a container selection.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software, depends upon the particular application, and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identification.

Clause 1. A medical device, comprising: a display device; and a controller configured to: provide a user interface configured to display a selectable list of disposables and configured for receiving a selection of a disposable from the selectable list for use in providing a therapy to a patient by the medical device; adjust, when an indication of a selected disposable is received, a first sensor or a motor associated with the medical device to provide the therapy to the patient, according to a characterization of the selected disposable; and receive, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

Clause 2. The medical device of Clause 1, wherein the medical device comprises an infusion pump and the therapy comprises an infusion of a fluid, wherein the controller is further configured to: automatically adjust a motor speed of the motor when the automated programming data selects the selected disposable, and wherein the motor speed is automatically adjusted based on the characterization of the selected disposable to satisfy a predetermined flow rate for the infusion.

Clause 3. The medical device of Clause 2, wherein the infusion pump is a syringe pump, wherein the controller is further configured to: receive the characterization from the automated programming data, wherein the characterization includes a size of a syringe to be used for the infusion, wherein the motor speed is automatically adjusted to control a speed of a syringe plunger based on the size of the syringe.

Clause 4. The medical device of Clause 2 or Clause 3, wherein the fluid is a medication and the automated programming data comprises a number of medication containers to fulfill a medication order associated with the patient, wherein the controller is further configured to: determine a current container number of a medication container loaded by the infusion pump; administer the medication to the patient from the medication container; when the medication within the medication container has been administered to the patient, determine, based on the current container number and the number of medication containers to fulfill the medication order, that a second container should be loaded by the infusion pump; and provide a user prompt, for display by the display device, to confirm loading of the second container.

Clause 5. The medical device of any one of Clauses 2 through 4, wherein the controller is further configured to: receive scanned information from a medication container that was scanned by a scanner associated with the infusion device; send the scanned information to the server with a request to obtain the automated programming data, wherein the automated programming data is received after the scanned information is sent to the server; receive, within the automated programming data, a drug identifier and a request to load parameters for a drug corresponding to the drug identifier from a memory of the infusion device; and load the parameters for the drug from the memory based on the drug identifier and the selected disposable; and administer the infusion to the patient based on the loaded parameters and the selected disposable.

Clause 6. The medical device of any one of Clauses 2 through 5, wherein the controller is further configured to: identify, using a second sensor, a disposable container loaded by the infusion pump; determine based on the selected disposable selected by the automated programming data, that the disposable container loaded by the infusion pump deviates from the selected disposable; and provide, for display by the display device, an indication that the disposable container loaded by the infusion pump deviates from the selected disposable.

Clause 7. The medical device of Clause 6, wherein the controller is further configured to: measure, using a second sensor, a size of the disposable container loaded by the infusion pump; receive, within the automated programming data, a size of the selected disposable; determine that the measured size of the disposable container does not match the received size of the selected disposable, wherein the indication that the disposable container loaded by the infusion pump deviates from the selected disposable is provided based on determining that the measured size does not match the received size.

Clause 8. The medical device of any one of Clauses 2 through 7, wherein the medical device comprises syringe pump and the therapy comprises an infusion of a fluid, wherein the controller is further configured to: receive the characterization from the automated programming data, wherein the characterization includes a size of a syringe to be used for the infusion; adjust the first sensor based on automatically adjusting a threshold for determining an occlusion alarm with the first sensor; measure, using the first sensor, a force exerted by a drive head of the syringe pump; and provide, for display by the display device, an indication of a deviation when the measured force satisfies the adjusted threshold.

Clause 9. A method performed by a medical device, comprising: providing, a user interface configured to display a selectable list of disposables and configured for receiving a selection of a disposable from the selectable list for use in providing a therapy to a patient by the medical device; adjusting, when an indication of a selected disposable is received, a first sensor or a motor associated with the medical device to provide the therapy to the patient, according to a characterization of the selected disposable; and receiving, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

Clause 10. The medical device of Clause 9, wherein the medical device comprises an infusion pump and the therapy comprises an infusion of a fluid, wherein the method further comprises: automatically adjusting a motor speed of the motor when the automated programming data selects the selected disposable, and wherein the motor speed is automatically adjusted based on the characterization of the selected disposable to satisfy a predetermined flow rate for the infusion.

Clause 11. The medical device of Clause 10, wherein the infusion pump is a syringe pump, wherein the method further comprises: receiving the characterization from the automated programming data, wherein the characterization includes a size of a syringe to be used for the infusion, wherein the motor speed is automatically adjusted to control a speed of a syringe plunger based on the size of the syringe.

Clause 12. The medical device of Clause 10 or Clause 11, wherein the fluid is a medication and the automated programming data comprises a number of medication containers to fulfill a medication order associated with the patient, wherein the method further comprises: determining a current container number of a medication container loaded by the infusion pump; administering the medication to the patient from the medication container; when the medication within the medication container has been administered to the patient, determining, based on the current container number and the number of medication containers to fulfill the medication order, that a second container should be loaded by the infusion pump; and providing a user prompt, for display by a display device, to confirm loading of the second container.

Clause 13. The medical device of any one of Clauses 10 through 12, wherein the method further comprises: receiving scanned information from a medication container that was scanned by a scanner associated with the infusion device; sending the scanned information to the server with a request to obtain the automated programming data, wherein the automated programming data is received after the scanned information is sent to the server; receiving, within the automated programming data, a drug identifier and a request to load parameters for a drug corresponding to the drug identifier from a memory of the infusion device; and loading the parameters for the drug from the memory based on the drug identifier and the selected disposable; and administering the infusion to the patient based on the loaded parameters and the selected disposable.

Clause 14. The medical device of any one of Clauses 10 through 13, wherein the method further comprises: identifying, using a second sensor, a disposable container loaded by the infusion pump; determining based on the selected disposable selected by the automated programming data, that the disposable container loaded by the infusion pump deviates from the selected disposable; and providing, for display by the display device, an indication that the disposable container loaded by the infusion pump deviates from the selected disposable.

Clause 15. The medical device of Clause 14, wherein the method further comprises: measuring, using a second sensor, a size of the disposable container loaded by the infusion pump; receiving, within the automated programming data, a size of the selected disposable; determining that the measured size of the disposable container does not match the received size of the selected disposable, wherein the indication that the disposable container loaded by the infusion pump deviates from the selected disposable is provided based on determining that the measured size does not match the received size.

Clause 16. The medical device of any one of Clauses 9 through 14, wherein the medical device comprises syringe pump and the therapy comprises an infusion of a fluid, wherein the method further comprises: receiving the characterization from the automated programming data, wherein the characterization includes a size of a syringe to be used for the infusion; adjusting the first sensor based on automatically adjusting a threshold for determining an occlusion alarm with the first sensor; measuring, using the first sensor, a force exerted by a drive head of the syringe pump; and providing, for display by a display device, an indication of a deviation when the measured force satisfies the adjusted threshold.

Clause 17. A non-transitory computer-readable medium having instructions stored thereon that, when executed by medical device, causes the medical device to perform operations comprising: providing, a user interface configured to display a selectable list of disposables and configured for receiving a selection of a disposable from the selectable list for use in providing a therapy to a patient by the medical device; adjusting, when an indication of a selected disposable is received, a first sensor or a motor associated with the medical device to provide the therapy to the patient, according to a characterization of the selected disposable; and receiving, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

Clause 18. The non-transitory computer-readable medium of Clause 17, wherein the medical device comprises an infusion pump and the therapy comprises an infusion of a fluid, wherein the operations further comprise: automatically adjusting a motor speed of the motor when the automated programming data selects the selected disposable, and wherein the motor speed is automatically adjusted based on the characterization of the selected disposable to satisfy a predetermined flow rate for the infusion.

Clause 19. The non-transitory computer-readable medium of Clause 17 or Clause 18, wherein the infusion pump is a syringe pump, wherein the operations further comprise: receiving the characterization from the automated programming data, wherein the characterization includes a size of a syringe to be used for the infusion, wherein the motor speed is automatically adjusted to control a speed of a syringe plunger based on the size of the syringe.

Clause 20. The non-transitory computer-readable medium of any one of Clauses 17 through 19, wherein the operations further comprise: identifying, using a second sensor, a disposable container loaded by the infusion pump; determining based on the selected disposable selected by the automated programming data, that the disposable container loaded by the infusion pump deviates from the selected disposable; and providing, for display by the display device, an indication that the disposable container loaded by the infusion pump deviates from the selected disposable.

Further Consideration:

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The predicate words "configured to", "operable to", and "programmed to" do not imply any particular tangible or intangible modification of a subject, but, rather, are intended to be used interchangeably. For example, a processor configured to monitor and control an operation, or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database, or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

What is claimed is:

1. A medical device, comprising:

a display device; and a controller configured to:

provide a user interface configured to display a selectable list of disposables and configured for receiving a selection of a disposable from the selectable list for use in providing a therapy to a patient by the medical device;

adjust, when an indication of a selected disposable is received, a first sensor or a motor associated with the medical device to provide the therapy to the patient, according to a characterization of the selected disposable; and receive, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

2. The medical device of claim 1, wherein the medical device comprises an infusion pump and the therapy comprises an infusion of a fluid, wherein the controller is further configured to:

automatically adjust a motor speed of the motor when the automated programming data selects the selected disposable, and wherein the motor speed is automatically adjusted based on the characterization of the selected disposable to satisfy a predetermined flow rate for the infusion.

3. The medical device of claim 2, wherein the infusion pump is a syringe pump, wherein the controller is further configured to:

receive the characterization from the automated programming data, wherein the characterization includes a size of a syringe to be used for the infusion, wherein the motor speed is automatically adjusted to control a speed of a syringe plunger based on the size of the syringe.

4. The medical device of claim 2, wherein the fluid is a medication and the automated programming data comprises a number of medication containers to fulfill a medication order associated with the patient, wherein the controller is further configured to:

determine a current container number of a medication container loaded by the infusion pump;

administer the medication to the patient from the medication container;

when the medication within the medication container has been administered to the patient, determine, based on the current container number and the number of medication containers to fulfill the medication order, that a second container should be loaded by the infusion pump; and provide a user prompt, for display by the display device, to confirm loading of the second container.

5. The medical device of claim 2, wherein the controller is further configured to:

receive scanned information from a medication container that was scanned by a scanner associated with the infusion device;

send the scanned information to the server with a request to obtain the automated programming data, wherein the automated programming data is received after the scanned information is sent to the server;

receive, within the automated programming data, a drug identifier and a request to load parameters for a drug corresponding to the drug identifier from a memory of the infusion device; and load the parameters for the drug from the memory based on the drug identifier and the selected disposable; and administer the infusion to the patient based on the loaded parameters and the selected disposable.

6. The medical device of claim 2, wherein the controller is further configured to:

identify, using a second sensor, a disposable container loaded by the infusion pump;

determine based on the selected disposable selected by the automated programming data, that the disposable container loaded by the infusion pump deviates from the selected disposable; and provide, for display by the display device, an indication that the disposable container loaded by the infusion pump deviates from the selected disposable.

7. The medical device of claim 6, wherein the controller is further configured to:

measure, using a second sensor, a size of the disposable container loaded by the infusion pump;

receive, within the automated programming data, a size of the selected disposable;

determine that the measured size of the disposable container does not match the received size of the selected disposable, wherein the indication that the disposable container loaded by the infusion pump deviates from the selected disposable is provided based on determining that the measured size does not match the received size.

8. The medical device of claim 2, wherein the medical device comprises syringe pump and the therapy comprises an infusion of a fluid, wherein the controller is further configured to:

receive the characterization from the automated programming data, wherein the characterization includes a size of a syringe to be used for the infusion;

adjust the first sensor based on automatically adjusting a threshold for determining an occlusion alarm with the first sensor;

measure, using the first sensor, a force exerted by a drive head of the syringe pump; and provide, for display by the display device, an indication of a deviation when the measured force satisfies the adjusted threshold.

9. A method performed by a medical device, comprising:

providing, a user interface configured to display a selectable list of disposables and configured for receiving a selection of a disposable from the selectable list for use in providing a therapy to a patient by the medical device;

adjusting, when an indication of a selected disposable is received, a first sensor or a motor associated with the medical device to provide the therapy to the patient, according to a characterization of the selected disposable; and receiving, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

10. The medical device of claim 9, wherein the medical device comprises an infusion pump and the therapy comprises an infusion of a fluid, wherein the method further comprises:

automatically adjusting a motor speed of the motor when the automated programming data selects the selected disposable, and wherein the motor speed is automatically adjusted based on the characterization of the selected disposable to satisfy a predetermined flow rate for the infusion.

11. The medical device of claim 10, wherein the infusion pump is a syringe pump, wherein the method further comprises:

receiving the characterization from the automated programming data, wherein the characterization includes a size of a syringe to be used for the infusion, wherein the motor speed is automatically adjusted to control a speed of a syringe plunger based on the size of the syringe.

12. The medical device of claim 10, wherein the fluid is a medication and the automated programming data comprises a number of medication containers to fulfill a medication order associated with the patient, wherein the method further comprises:

determining a current container number of a medication container loaded by the infusion pump;

administering the medication to the patient from the medication container;

when the medication within the medication container has been administered to the patient, determining, based on the current container number and the number of medication containers to fulfill the medication order, that a second container should be loaded by the infusion pump; and providing a user prompt, for display by a display device, to confirm loading of the second container.

13. The medical device of claim 10, wherein the method further comprises:

receiving scanned information from a medication container that was scanned by a scanner associated with the infusion device;

sending the scanned information to the server with a request to obtain the automated programming data, wherein the automated programming data is received after the scanned information is sent to the server;

receiving, within the automated programming data, a drug identifier and a request to load parameters for a drug corresponding to the drug identifier from a memory of the infusion device; and loading the parameters for the drug from the memory based on the drug identifier and the selected disposable; and administering the infusion to the patient based on the loaded parameters and the selected disposable.

14. The medical device of claim 10, wherein the method further comprises:

identifying, using a second sensor, a disposable container loaded by the infusion pump;

determining based on the selected disposable selected by the automated programming data, that the disposable container loaded by the infusion pump deviates from the selected disposable; and providing, for display by the display device, an indication that the disposable container loaded by the infusion pump deviates from the selected disposable.

15. The medical device of claim 14, wherein the method further comprises:

measuring, using a second sensor, a size of the disposable container loaded by the infusion pump;

receiving, within the automated programming data, a size of the selected disposable;

determining that the measured size of the disposable container does not match the received size of the selected disposable, wherein the indication that the disposable container loaded by the infusion pump deviates from the selected disposable is provided based on determining that the measured size does not match the received size.

16. The medical device of claim 9, wherein the medical device comprises syringe pump and the therapy comprises an infusion of a fluid, wherein the method further comprises:

receiving the characterization from the automated programming data, wherein the characterization includes a size of a syringe to be used for the infusion;

adjusting the first sensor based on automatically adjusting a threshold for determining an occlusion alarm with the first sensor;

measuring, using the first sensor, a force exerted by a drive head of the syringe pump; and providing, for display by a display device, an indication of a deviation when the measured force satisfies the adjusted threshold.

17. A non-transitory computer-readable medium having instructions stored thereon that, when executed by medical device, causes the medical device to perform operations comprising:

providing, a user interface configured to display a selectable list of disposables and configured for receiving a selection of a disposable from the selectable list for use in providing a therapy to a patient by the medical device;

adjusting, when an indication of a selected disposable is received, a first sensor or a motor associated with the medical device to provide the therapy to the patient, according to a characterization of the selected disposable; and receiving, from a server remote from the medical device, automated programming data configured to instruct the medical device regarding the therapy to the patient and to select the selected disposable for use in the therapy according to a medical order for the patient, wherein the selectable list of disposables is displayed by the user interface when the automated programming data selecting the selected disposable is not received by the controller, and the selectable list of disposables is bypassed and not displayed when the automated programming data is received and selects the selected disposable.

18. The non-transitory computer-readable medium of claim 17, wherein the medical device comprises an infusion pump and the therapy comprises an infusion of a fluid, wherein the operations further comprise:

automatically adjusting a motor speed of the motor when the automated programming data selects the selected disposable, and wherein the motor speed is automatically adjusted based on the characterization of the selected disposable to satisfy a predetermined flow rate for the infusion.

19. The non-transitory computer-readable medium of claim 17, wherein the infusion pump is a syringe pump, wherein the operations further comprise:

receiving the characterization from the automated programming data, wherein the characterization includes a size of a syringe to be used for the infusion, wherein the motor speed is automatically adjusted to control a speed of a syringe plunger based on the size of the syringe.

20. The non-transitory computer-readable medium of claim 17, wherein the operations further comprise:

identifying, using a second sensor, a disposable container loaded by the infusion pump;

determining based on the selected disposable selected by the automated programming data, that the disposable container loaded by the infusion pump deviates from the selected disposable; and providing, for display by the display device, an indication that the disposable container loaded by the infusion pump deviates from the selected disposable.

* * * * *